US008460710B2

(12) United States Patent
Burnside et al.

(10) Patent No.: US 8,460,710 B2
(45) Date of Patent: *Jun. 11, 2013

(54) ANTIBIOTIC PRODUCT, USE AND FORMULATION THEREOF

(75) Inventors: Beth A. Burnside, Bethesda, MD (US); Henry H. Flanner, Montgomery Village, MD (US); Colin Rowlings, Potomac, MD (US)

(73) Assignee: Shionogi, Inc., Florham Park, NJ (US)

( * ) Notice: Subject to any disclaimer, the term of this patent is extended or adjusted under 35 U.S.C. 154(b) by 1151 days.

This patent is subject to a terminal disclaimer.

(21) Appl. No.: 10/940,265

(22) Filed: Sep. 14, 2004

(65) Prior Publication Data

US 2005/0058708 A1  Mar. 17, 2005

Related U.S. Application Data

(60) Provisional application No. 60/503,041, filed on Sep. 15, 2003.

(51) Int. Cl.
*A61K 9/16* (2006.01)
*A61K 9/22* (2006.01)
*A61K 9/26* (2006.01)
*A61K 9/52* (2006.01)
*A61K 9/54* (2006.01)

(52) U.S. Cl.
USPC ........... 424/490; 424/457; 424/458; 424/468; 424/469

(58) Field of Classification Search
USPC .......................... 424/457, 458, 468, 469, 590
See application file for complete search history.

(56) References Cited

U.S. PATENT DOCUMENTS

| | | | |
|---|---|---|---|
| 3,108,046 A | 10/1963 | Harbit | 167/82 |
| 3,870,790 A | 3/1975 | Lowey et al. | 424/19 |
| 4,007,174 A | 2/1977 | Laundon | 260/243 |
| 4,008,246 A | 2/1977 | Ochiai et al. | 260/306.8 |
| 4,018,918 A | 4/1977 | Ayer et al. | 514/24 |
| 4,048,306 A | 9/1977 | Maier et al. | 424/180 |
| 4,131,672 A | 12/1978 | Huffman | 514/204 |
| 4,175,125 A | 11/1979 | Huffman | 514/208 |
| 4,226,849 A | 10/1980 | Schor | 424/19 |
| 4,236,211 A | 11/1980 | Arvesen | 435/32 |
| 4,250,166 A | 2/1981 | Maekawa et al. | 424/81 |
| 4,331,803 A | 5/1982 | Watanabe et al. | 536/7.2 |
| 4,362,731 A | 12/1982 | Hill | 424/256 |
| 4,369,172 A | 1/1983 | Schor et al. | 424/19 |
| 4,399,151 A | 8/1983 | Sjoerdsma et al. | 514/564 |
| 4,430,495 A | 2/1984 | Patt et al. | 536/16.3 |
| 4,435,173 A | 3/1984 | Siposs et al. | 609/155 |
| 4,474,768 A | 10/1984 | Bright | 424/180 |
| 4,517,359 A | 5/1985 | Kobrehel et al. | 536/7.4 |
| 4,525,352 A | 6/1985 | Cole et al. | 424/114 |
| 4,529,720 A | 7/1985 | Cole et al. | 514/191 |
| 4,560,552 A | 12/1985 | Cole et al. | 424/114 |
| 4,568,741 A | 2/1986 | Livingston | 536/16.5 |
| 4,598,045 A | 7/1986 | Masover et al. | 435/34 |
| 4,616,008 A | 10/1986 | Hirai et al. | 514/200 |
| 4,634,697 A | 1/1987 | Hamashima | 514/202 |
| 4,644,031 A | 2/1987 | Lehmann et al. | 524/501 |
| 4,670,549 A | 6/1987 | Morimoto et al. | 536/7.4 |
| 4,672,109 A | 6/1987 | Watanabe et al. | 536/7.2 |
| 4,680,386 A | 7/1987 | Morimoto et al. | 536/7.4 |
| 4,710,565 A | 12/1987 | Livingston et al. | 536/16.5 |
| 4,723,958 A | 2/1988 | Pope et al. | 604/890.1 |
| 4,728,512 A | 3/1988 | Mehta et al. | 424/458 |
| 4,749,568 A | 6/1988 | Reusser et al. | 424/119 |
| 4,755,385 A | 7/1988 | Etienne et al. | 424/154 |
| 4,775,751 A | 10/1988 | McShane | 540/230 |
| 4,794,001 A | 12/1988 | Mehta et al. | 424/458 |
| 4,808,411 A | 2/1989 | Lu et al. | 424/441 |
| 4,812,561 A | 3/1989 | Hamashima et al. | 540/222 |
| 4,828,836 A | 5/1989 | Elger et al. | 424/419 |
| 4,831,025 A | 5/1989 | Godtfredsen et al. | 514/195 |
| 4,835,140 A | 5/1989 | Smith et al. | 514/24 |
| 4,842,866 A | 6/1989 | Horder et al. | 424/468 |
| 4,849,515 A | 7/1989 | Matier et al. | 536/16.5 |
| 4,863,741 A * | 9/1989 | Becker | 424/465 |
| 4,879,135 A | 11/1989 | Greco et al. | 623/1.48 |
| 4,894,119 A | 1/1990 | Baron, Jr. et al. | 162/168.2 |
| 4,895,934 A | 1/1990 | Matier et al. | 536/16.5 |
| 4,904,476 A | 2/1990 | Mehta et al. | 424/456 |
| 4,915,953 A | 4/1990 | Jordan et al. | 424/473 |
| 4,945,080 A | 7/1990 | Lindstrom et al. | 514/29 |
| 4,945,405 A | 7/1990 | Hirota | 358/516 |
| 4,971,805 A | 11/1990 | Kitanishi et al. | 424/494 |
| 4,990,602 A | 2/1991 | Morimoto et al. | 536/7.4 |
| 5,011,692 A | 4/1991 | Fujioka et al. | 424/426 |
| 5,045,533 A | 9/1991 | Philippe et al. | 514/29 |
| 5,051,262 A | 9/1991 | Panoz et al. | 424/468 |
| 5,110,597 A | 5/1992 | Wong et al. | 424/438 |
| 5,110,598 A | 5/1992 | Kwan et al. | 424/438 |
| 5,143,661 A | 9/1992 | Lawter et al. | 264/4.3 |
| 5,158,777 A | 10/1992 | Abramowitz et al. | 424/458 |
| 5,178,874 A | 1/1993 | Kwan et al. | 424/438 |

(Continued)

FOREIGN PATENT DOCUMENTS

| | | |
|---|---|---|
| EP | 0052075 | 11/1981 |
| EP | 0293885 | 12/1988 |

(Continued)

OTHER PUBLICATIONS

"Goodman & Gilman's The Pharmacological Basis of Therapeutics, 10th ed." Hardman JG, Limbird LE, and Gilman AG, Eds., McGraw-Hill, 2001, pp. 1148, 1928, and 2019.*

(Continued)

*Primary Examiner* — Paul Zarek
(74) *Attorney, Agent, or Firm* — MH2 Technology Law Group, LLP

(57) ABSTRACT

An antibiotic product is comprised of at least three dosage forms, each of which has a different release profile, with the $C_{max}$ for the antibiotic product being reached in less than about twelve hours after the initial release of antibiotic. In one embodiment, there are two delayed release dosage forms, as well as a delayed sustained release dosage form, with each of the dosage forms having a different release profile, wherein each reaches a $C_{max}$ at different times.

37 Claims, No Drawings

U.S. PATENT DOCUMENTS

| | | | |
|---|---|---|---|
| 5,182,374 A | 1/1993 | Tobkes et al. | 536/16.5 |
| 5,204,055 A | 4/1993 | Sachs et al. | 419/2 |
| 5,213,808 A | 5/1993 | Bar-Shalom et al. | 424/473 |
| 5,229,131 A | 7/1993 | Amidon et al. | 424/451 |
| 5,230,703 A | 7/1993 | Alon | 604/20 |
| 5,274,085 A | 12/1993 | Amano et al. | 536/7.4 |
| 5,288,503 A | 2/1994 | Wood et al. | 424/497 |
| 5,334,590 A | 8/1994 | DiNinno et al. | 514/210.09 |
| 5,340,656 A | 8/1994 | Sachs et al. | 428/546 |
| 5,358,713 A | 10/1994 | Shimamura | 424/729 |
| 5,387,380 A | 2/1995 | Cima et al. | 264/69 |
| 5,393,765 A | 2/1995 | Infeld et al. | 514/365 |
| 5,395,626 A | 3/1995 | Kotwal et al. | 424/472 |
| 5,395,628 A | 3/1995 | Noda et al. | 424/490 |
| 5,399,723 A | 3/1995 | Iinuma et al. | 549/403 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,422,343 A | 6/1995 | Yamamoto et al. | 514/45 |
| 5,430,021 A | 7/1995 | Rudnic et al. | 514/14 |
| 5,445,829 A | 8/1995 | Paradissis et al. | 424/480 |
| 5,457,187 A | 10/1995 | Gmeiner et al. | 536/25.5 |
| 5,462,747 A | 10/1995 | Radebaugh et al. | 424/465 |
| 5,466,446 A | 11/1995 | Stiefel et al. | 424/78.37 |
| 5,472,708 A | 12/1995 | Chen | 424/451 |
| 5,476,854 A | 12/1995 | Young | 514/254 |
| 5,490,962 A | 2/1996 | Cima et al. | 264/22 |
| 5,508,040 A | 4/1996 | Chen | 424/451 |
| 5,518,680 A | 5/1996 | Cima et al. | 264/401 |
| 5,538,954 A | 7/1996 | Koch et al. | 514/53 |
| 5,543,417 A | 8/1996 | Waldstreicher | 514/284 |
| 5,556,839 A | 9/1996 | Greene et al. | 514/29 |
| 5,567,441 A | 10/1996 | Chen | 424/494 |
| 5,576,022 A | 11/1996 | Yang et al. | 424/472 |
| 5,578,713 A | 11/1996 | McGill, III | 536/18.5 |
| 5,599,557 A | 2/1997 | Johnson et al. | 424/500 |
| 5,607,685 A | 3/1997 | Cimbollek et al. | 424/422 |
| 5,633,006 A | 5/1997 | Catania et al. | 424/441 |
| 5,672,359 A | 9/1997 | Digenis et al. | 424/463 |
| 5,688,516 A | 11/1997 | Raad et al. | 424/409 |
| 5,702,895 A | 12/1997 | Matsunaga et al. | 435/6 |
| 5,705,190 A | 1/1998 | Broad et al. | 424/465 |
| 5,707,646 A | 1/1998 | Yajima et al. | 424/439 |
| 5,719,132 A | 2/1998 | Lin et al. | 514/50 |
| 5,719,272 A | 2/1998 | Yang et al. | 536/7.4 |
| 5,725,553 A | 3/1998 | Moenning | 606/213 |
| 5,733,886 A | 3/1998 | Baroody et al. | 514/24 |
| 5,756,473 A | 5/1998 | Liu et al. | 514/29 |
| 5,780,446 A | 7/1998 | Ramu | 514/34 |
| 5,789,584 A | 8/1998 | Christensen et al. | 540/227 |
| 5,808,017 A | 9/1998 | Chang | 536/7.4 |
| 5,817,321 A | 10/1998 | Alakhov et al. | 424/400 |
| 5,827,531 A | 10/1998 | Morrison et al. | 424/450 |
| 5,837,284 A | 11/1998 | Mehta et al. | 424/459 |
| 5,837,829 A | 11/1998 | Ku | 536/7.4 |
| 5,840,329 A | 11/1998 | Bai | 424/458 |
| 5,840,760 A | 11/1998 | Carraher, Jr. et al. | 514/493 |
| 5,844,105 A | 12/1998 | Liu et al. | 536/18.5 |
| 5,849,776 A | 12/1998 | Czernielewski et al. | 514/398 |
| 5,852,180 A | 12/1998 | Patel | 536/7.4 |
| 5,858,986 A | 1/1999 | Liu et al. | 514/29 |
| 5,864,023 A | 1/1999 | Ku et al. | 536/7.2 |
| 5,869,170 A | 2/1999 | Cima et al. | 428/304.4 |
| 5,872,104 A | 2/1999 | Vermeulen et al. | 514/29 |
| 5,872,229 A | 2/1999 | Liu et al. | 536/18.6 |
| 5,877,243 A | 3/1999 | Sarangapani | 524/139 |
| 5,883,079 A | 3/1999 | Zopf et al. | 514/25 |
| 5,892,008 A | 4/1999 | Ku et al. | 536/18.5 |
| 5,910,322 A | 6/1999 | Rivett et al. | 424/484 |
| 5,919,219 A | 7/1999 | Knowlton | 607/102 |
| 5,919,489 A | 7/1999 | Saleki-Gerhardt et al. | 424/501 |
| 5,919,916 A | 7/1999 | Gracey et al. | 536/7.2 |
| 5,929,219 A | 7/1999 | Hill | 536/7.2 |
| 5,932,710 A | 8/1999 | Liu et al. | 536/18.7 |
| 5,945,124 A | 8/1999 | Sachs et al. | 424/472 |
| 5,945,405 A | 8/1999 | Spanton et al. | 514/29 |
| 5,972,373 A | 10/1999 | Yajima et al. | 424/439 |
| 5,980,942 A | 11/1999 | Katzhendler et al. | 424/465 |
| 5,985,643 A | 11/1999 | Tomasz et al. | 435/243 |
| 5,998,194 A | 12/1999 | Summers, Jr. et al. | 435/252.33 |
| 6,008,195 A | 12/1999 | Selsted | 514/14 |
| 6,010,718 A | 1/2000 | Al-Razzak et al. | 424/464 |
| 6,013,507 A | 1/2000 | Tomasz et al. | 435/252.3 |
| 6,027,748 A | 2/2000 | Conte et al. | 424/458 |
| 6,031,093 A | 2/2000 | Cole et al. | 540/349 |
| 6,048,977 A | 4/2000 | Cole et al. | 540/349 |
| 6,051,255 A | 4/2000 | Conley et al. | 424/482 |
| 6,051,703 A | 4/2000 | Cole et al. | 514/210.06 |
| 6,057,291 A | 5/2000 | Hancock et al. | 514/12 |
| 6,059,816 A | 5/2000 | Moenning | 606/213 |
| 6,063,613 A | 5/2000 | De Lencastre et al. | 435/252.3 |
| 6,063,917 A | 5/2000 | Ascher et al. | 540/217 |
| 6,068,859 A | 5/2000 | Curatolo et al. | 424/490 |
| 6,110,925 A | 8/2000 | Williams et al. | 514/272 |
| 6,117,843 A | 9/2000 | Baroody et al. | 514/24 |
| 6,120,803 A | 9/2000 | Wong et al. | 424/473 |
| 6,127,349 A | 10/2000 | Chasalow | 514/77 |
| 6,132,768 A | 10/2000 | Sachs et al. | 424/458 |
| 6,132,771 A | 10/2000 | Depui et al. | 424/468 |
| 6,136,587 A | 10/2000 | Tomasz et al. | 435/252.3 |
| 6,156,507 A | 12/2000 | Hiramatsu et al. | 435/6 |
| 6,159,491 A | 12/2000 | Durrani | 424/430 |
| 6,162,925 A | 12/2000 | Williams et al. | 548/335.5 |
| 6,183,778 B1 | 2/2001 | Conte et al. | 424/472 |
| 6,187,768 B1 | 2/2001 | Welle et al. | 514/199 |
| 6,214,359 B1 | 4/2001 | Bax | 424/400 |
| 6,218,380 B1 | 4/2001 | Cole et al. | 514/210.06 |
| 6,228,398 B1 | 5/2001 | Devane et al. | 424/484 |
| 6,231,875 B1 | 5/2001 | Sun et al. | 424/401 |
| 6,248,363 B1 | 6/2001 | Patel et al. | 424/497 |
| 6,251,647 B1 | 6/2001 | De Lencastre et al. | 435/193 |
| 6,265,394 B1 | 7/2001 | Sterzycki et al. | 514/203 |
| 6,270,805 B1 | 8/2001 | Chen et al. | 424/497 |
| 6,280,771 B1 | 8/2001 | Monkhouse et al. | 424/484 |
| 6,294,199 B1 | 9/2001 | Conley et al. | 424/468 |
| 6,294,526 B1 | 9/2001 | Higuchi et al. | 514/192 |
| 6,296,873 B1 | 10/2001 | Katzhendler et al. | 424/465 |
| 6,297,215 B1 | 10/2001 | Hancock et al. | 514/12 |
| 6,299,903 B1 | 10/2001 | Rivett et al. | 424/464 |
| 6,306,436 B1 | 10/2001 | Chungi et al. | 424/464 |
| 6,309,663 B1 | 10/2001 | Patel et al. | 424/450 |
| 6,322,819 B1 | 11/2001 | Burnside et al. | 424/494 |
| 6,333,050 B2 | 12/2001 | Wong et al. | 424/473 |
| 6,340,475 B2 | 1/2002 | Shell et al. | 424/469 |
| 6,352,720 B1 | 3/2002 | Martin et al. | 424/464 |
| 6,358,525 B1 | 3/2002 | Guo et al. | 424/464 |
| 6,358,528 B1 | 3/2002 | Grimmett et al. | 424/474 |
| 6,383,471 B1 | 5/2002 | Chen et al. | 424/45 |
| 6,384,081 B2 | 5/2002 | Berman | 514/621 |
| 6,391,614 B1 | 5/2002 | Tomasz et al. | 435/253.2 |
| 6,399,086 B1 | 6/2002 | Katzhendler et al. | 424/405 |
| 6,403,569 B1 | 6/2002 | Achterrath | 514/50 |
| 6,406,717 B2 | 6/2002 | Cherukuri | 424/484 |
| 6,406,880 B1 | 6/2002 | Thornton | 435/32 |
| 6,440,462 B1 | 8/2002 | Raneburger et al. | 424/489 |
| 6,444,796 B1 | 9/2002 | Suh et al. | 536/7.2 |
| 6,468,964 B1 | 10/2002 | Rowe | 514/6 |
| 6,479,496 B1 | 11/2002 | Wolff | 514/252.17 |
| 6,495,157 B1 | 12/2002 | Pena et al. | 424/433 |
| 6,497,901 B1 | 12/2002 | Royer | 424/468 |
| 6,503,709 B1 | 1/2003 | Bekkaoui et al. | 435/6 |
| 6,506,886 B1 | 1/2003 | Lee et al. | 536/7.2 |
| 6,514,518 B2 | 2/2003 | Monkhouse et al. | 424/427 |
| 6,515,010 B1 | 2/2003 | Franchini et al. | 514/411 |
| 6,515,116 B2 | 2/2003 | Suh et al. | 536/7.2 |
| 6,530,958 B1 | 3/2003 | Cima et al. | 623/23.51 |
| 6,541,014 B2 | 4/2003 | Rudnic et al. | 424/400 |
| 6,544,555 B2 | 4/2003 | Rudnic et al. | 424/468 |
| 6,548,084 B2 | 4/2003 | Leonard et al. | 424/482 |
| 6,550,955 B2 | 4/2003 | D'Silva | 366/130 |
| 6,551,584 B2 | 4/2003 | Bandyopadhyay et al. | 424/78.04 |
| 6,551,616 B1 | 4/2003 | Notario et al. | 424/464 |
| 6,558,699 B2 | 5/2003 | Venkatesh | 424/464 |
| 6,565,873 B1 | 5/2003 | Shefer et al. | 424/426 |
| 6,565,882 B2 | 5/2003 | Rudnic | 424/472 |
| 6,569,463 B2 | 5/2003 | Patel et al. | 424/497 |

| | | | | | | | |
|---|---|---|---|---|---|---|---|
| 6,585,997 B2 | 7/2003 | Moro et al. | 424/434 | 2003/0091627 A1 | 5/2003 | Sharma | 424/465 |
| 6,599,884 B2 | 7/2003 | Avrutov et al. | 514/29 | 2003/0096006 A1 | 5/2003 | Rudnic et al. | 424/468 |
| 6,605,069 B1 | 8/2003 | Albers et al. | 604/264 | 2003/0096007 A1 | 5/2003 | Rudnic et al. | 424/468 |
| 6,605,300 B1 | 8/2003 | Burnside et al. | 424/452 | 2003/0096008 A1 | 5/2003 | Rudnic et al. | 424/468 |
| 6,605,609 B2 | 8/2003 | Barbachyn et al. | 514/227.8 | 2003/0099706 A1 | 5/2003 | Rudnic et al. | 424/468 |
| 6,605,751 B1 | 8/2003 | Gibbins et al. | 602/41 | 2003/0099707 A1 | 5/2003 | Rudnic et al. | 424/468 |
| 6,610,323 B1 | 8/2003 | Lundberg et al. | 424/458 | 2003/0104054 A1 | 6/2003 | Rudnic et al. | 424/468 |
| 6,610,328 B2 | 8/2003 | Rudnic et al. | 424/468 | 2003/0104055 A1 | 6/2003 | Rudnic et al. | 424/468 |
| 6,617,436 B2 | 9/2003 | Avrutov et al. | 536/7.2 | 2003/0104056 A1 | 6/2003 | Rudnic et al. | 424/468 |
| 6,623,757 B2 | 9/2003 | Rudnic et al. | 424/468 | 2003/0104058 A1 | 6/2003 | Rudnic et al. | 424/468 |
| 6,623,758 B2 | 9/2003 | Rudnic et al. | 424/468 | 2003/0124196 A1 | 7/2003 | Weinbach et al. | 424/499 |
| 6,624,292 B2 | 9/2003 | Lifshitz et al. | 536/7.2 | 2003/0129236 A1 | 7/2003 | Heimlich et al. | 424/470 |
| 6,627,222 B2 | 9/2003 | Rudnic et al. | 424/468 | 2003/0143268 A1 | 7/2003 | Pryce Lewis et al. | 424/464 |
| 6,627,743 B1 | 9/2003 | Liu et al. | 536/7.2 | 2003/0147953 A1 | 8/2003 | Rudnic et al. | 424/468 |
| 6,630,498 B2 | 10/2003 | Gudipati et al. | 514/397 | 2003/0152627 A1 | 8/2003 | Beckert et al. | |
| 6,632,453 B2 | 10/2003 | Rudnic et al. | 424/468 | 2003/0190360 A1 | 10/2003 | Baichwal et al. | 424/470 |
| 6,635,280 B2 | 10/2003 | Shell et al. | 424/469 | 2003/0198677 A1 | 10/2003 | Pryce Lewis et al. | 424/471 |
| 6,638,532 B2 | 10/2003 | Rudnic et al. | 424/468 | 2003/0199808 A1 | 10/2003 | Henley et al. | 604/20 |
| 6,642,276 B2 | 11/2003 | Wadhwa | 514/781 | 2003/0203023 A1 | 10/2003 | Rudnic et al. | 424/468 |
| 6,663,890 B2 | 12/2003 | Rudnic et al. | 424/468 | 2003/0206951 A1 | 11/2003 | Rudnic et al. | 424/468 |
| 6,663,891 B2 | 12/2003 | Rudnic et al. | 424/468 | 2003/0216555 A1 | 11/2003 | Lifshitz et al. | 536/7.1 |
| 6,667,042 B2 | 12/2003 | Rudnic et al. | 424/400 | 2003/0216556 A1 | 11/2003 | Avrutov et al. | 536/7.2 |
| 6,667,057 B2 | 12/2003 | Rudnic et al. | 424/468 | 2003/0232089 A1 | 12/2003 | Singh et al. | 424/488 |
| 6,669,948 B2 | 12/2003 | Rudnic et al. | 424/400 | 2003/0235615 A1 | 12/2003 | Rudnic | 424/468 |
| 6,669,955 B2 | 12/2003 | Chungi et al. | 424/464 | 2004/0018234 A1 | 1/2004 | Rudnic et al. | 424/468 |
| 6,673,369 B2 | 1/2004 | Rampal et al. | 424/468 | 2004/0033262 A1 | 2/2004 | Kshirsagar et al. | 424/468 |
| 6,682,759 B2 | 1/2004 | Lim et al. | 424/468 | 2004/0043073 A1 | 3/2004 | Chen et al. | 424/486 |
| 6,696,426 B2 | 2/2004 | Singh et al. | 514/58 | 2004/0047906 A1 | 3/2004 | Percel et al. | 424/468 |
| 6,702,803 B2 | 3/2004 | Kupperblatt et al. | 604/890.1 | 2004/0048814 A1 | 3/2004 | Vanderbist et al. | 514/29 |
| 6,706,273 B1 | 3/2004 | Roessler | 424/422 | 2004/0052842 A1 | 3/2004 | Rudnic et al. | 424/468 |
| 6,723,340 B2 | 4/2004 | Gusler et al. | 424/468 | 2004/0058879 A1 | 3/2004 | Avrutov et al. | 514/29 |
| 6,723,341 B2 | 4/2004 | Rudnic et al. | 424/468 | 2004/0091528 A1 | 5/2004 | Rogers et al. | 424/468 |
| 6,730,320 B2 | 5/2004 | Rudnic et al. | 424/468 | 2004/0126427 A1 | 7/2004 | Venkatesh et al. | 424/469 |
| 6,730,325 B2 | 5/2004 | Devane et al. | 424/489 | 2004/0176737 A1 | 9/2004 | Henley et al. | 604/501 |
| 6,735,470 B2 | 5/2004 | Henley et al. | 604/20 | 2004/0219223 A1 | 11/2004 | Kunz | 424/489 |
| 6,740,664 B2 | 5/2004 | Cagle et al. | 514/311 | 2004/0253249 A1 | 12/2004 | Rudnic et al. | 424/184.1 |
| 6,746,692 B2 | 6/2004 | Conley et al. | 424/468 | 2004/0265379 A1 | 12/2004 | Conley et al. | 424/465 |
| 6,756,057 B2 | 6/2004 | Storm et al. | 424/472 | 2005/0019403 A1* | 1/2005 | Burnside et al. | 424/468 |
| 6,767,899 B1 | 7/2004 | Kay et al. | 514/62 | 2005/0053658 A1 | 3/2005 | Venkatesh et al. | 424/468 |
| 6,777,420 B2 | 8/2004 | Zhi et al. | 514/272 | 2005/0064033 A1 | 3/2005 | Notario et al. | 424/468 |
| 6,783,773 B1 | 8/2004 | Storm et al. | 424/468 | 2005/0064034 A1 | 3/2005 | Li et al. | 424/469 |
| 6,818,407 B2 | 11/2004 | Hancock et al. | 435/7.1 | 2005/0163857 A1 | 7/2005 | Rampal et al. | 424/489 |
| 6,824,792 B2 | 11/2004 | Foreman et al. | 424/487 | 2005/0203076 A1 | 9/2005 | Li et al. | 514/183 |
| 6,872,407 B2 | 3/2005 | Notario et al. | 424/464 | 2005/0203085 A1 | 9/2005 | Li et al. | 514/224.5 |
| 6,878,387 B1 | 4/2005 | Petereit et al. | 424/490 | 2005/0209210 A1 | 9/2005 | Ding et al. | 514/183 |
| 6,906,035 B2 | 6/2005 | Hancock et al. | 514/12 | 2005/0238714 A1 | 10/2005 | Rudnic et al. | 424/468 |
| 6,929,804 B2 | 8/2005 | Rudnic et al. | 424/468 | 2005/0256096 A1 | 11/2005 | Combrink et al. | 514/183 |
| 6,946,458 B2 | 9/2005 | Turos | 514/210.15 | 2005/0261262 A1 | 11/2005 | Ma et al. | 514/183 |
| 6,984,401 B2 | 1/2006 | Rudnic et al. | 424/489 | 2005/0277633 A1 | 12/2005 | Ma et al. | 514/224.5 |
| 6,991,807 B2 | 1/2006 | Rudnic et al. | 424/468 | 2006/0019985 A1 | 1/2006 | Ma et al. | 514/306 |
| 7,008,633 B2 | 3/2006 | Yang et al. | 424/422 | 2006/0019986 A1 | 1/2006 | Ding et al. | 514/306 |
| 2001/0046984 A1 | 11/2001 | Rudnic | 514/210.09 | 2006/0111302 A1 | 5/2006 | Romesberg et al. | 514/18 |
| 2001/0048944 A1 | 12/2001 | Rudnic et al. | 424/468 | | | | |
| 2002/0004070 A1 | 1/2002 | Rudnic et al. | 424/468 | | | | |
| 2002/0004499 A1 | 1/2002 | Rudnic et al. | 514/192 | | | | |
| 2002/0015728 A1 | 2/2002 | Payumo et al. | 424/451 | | | | |
| 2002/0028920 A1 | 3/2002 | Lifshitz et al. | 536/7.1 | | | | |
| 2002/0042394 A1 | 4/2002 | Hogenkamp et al. | 514/53 | | | | |
| 2002/0068078 A1 | 6/2002 | Rudnic et al. | 424/408 | | | | |
| 2002/0068085 A1 | 6/2002 | Rudnic et al. | 424/468 | | | | |
| 2002/0081332 A1 | 6/2002 | Rampal et al. | 424/461 | | | | |
| 2002/0103261 A1 | 8/2002 | Ninkov | 514/731 | | | | |
| 2002/0106412 A1 | 8/2002 | Rowe et al. | 424/490 | | | | |
| 2002/0115624 A1 | 8/2002 | Behar et al. | 514/42 | | | | |
| 2002/0119168 A1 | 8/2002 | Rudnic et al. | 424/400 | | | | |
| 2002/0136764 A1 | 9/2002 | Rudnic et al. | 424/457 | | | | |
| 2002/0136765 A1 | 9/2002 | Rudnic et al. | 424/457 | | | | |
| 2002/0136766 A1 | 9/2002 | Rudnic et al. | 424/457 | | | | |
| 2002/0150619 A1 | 10/2002 | Rudnic et al. | 424/468 | | | | |
| 2002/0197314 A1 | 12/2002 | Rudnic et al. | 424/468 | | | | |
| 2003/0012814 A1 | 1/2003 | Rudnic et al. | 424/468 | | | | |
| 2003/0018295 A1 | 1/2003 | Henley et al. | 604/20 | | | | |
| 2003/0049311 A1 | 3/2003 | McAllister et al. | 424/452 | | | | |
| 2003/0064100 A1 | 4/2003 | Rudnic et al. | 424/468 | | | | |
| 2003/0073647 A1 | 4/2003 | Chao et al. | 514/42 | | | | |
| 2003/0073648 A1 | 4/2003 | Chao et al. | 514/42 | | | | |
| 2003/0073826 A1 | 4/2003 | Chao et al. | 536/18.7 | | | | |
| 2003/0077323 A1 | 4/2003 | Rudnic et al. | 424/468 | | | | |
| 2003/0086969 A1 | 5/2003 | Rudnic et al. | 424/468 | | | | |

FOREIGN PATENT DOCUMENTS

| | | | |
|---|---|---|---|
| EP | 0418565 A2 | 3/1991 |
| EP | 0436370 | 7/1991 |
| EP | 0652008 | 5/1995 |
| FR | 2585948 | 2/1982 |
| GB | 2087235 | 5/1982 |
| WO | WO 90/08537 | 8/1990 |
| WO | WO 94/27557 | 12/1994 |
| WO | WO 95/20946 | 8/1995 |
| WO | WO 95/30422 | 11/1995 |
| WO | WO 96/04908 | 2/1996 |
| WO | WO 97/22335 | 6/1997 |
| WO | WO 97/43277 | 11/1997 |
| WO | WO 98/22091 | 5/1998 |
| WO | WO 98/46239 | 10/1998 |
| WO | WO-98-51287 A1 | 11/1998 |
| WO | WO 99/03453 | 1/1999 |
| WO | WO 99/40097 | 8/1999 |
| WO | WO 00/48607 | 8/2000 |
| WO | WO 00/61116 | 10/2000 |
| WO | WO-01-13895 A2 | 3/2001 |
| WO | WO 01/26663 | 4/2001 |
| WO | WO 02/38577 | 5/2002 |
| WO | WO 03/029439 | 4/2003 |
| WO | WO 2005/056754 | 6/2005 |
| WO | WO 2005/070941 | 8/2005 |

OTHER PUBLICATIONS

Mitscher LA, Chapter 34 Antibiotics and Antimicrobial Agents, "Foye's Principles of Medicinal Chemistry, 5th ed." Williams DA and Lemke TL Eds., Lippincott Williams & Wilkins, 2002, 819-866 (pp. 819, 834-836, and 842-844 provided).*
Erah PO, Goddard AF, Barrett DA, Shaw PN, Spiller RC. The stability of amoxycillin, clarithromycin and metronidazole in gastric juice: relevance to the treatment of *Helicobacter pylori* infection. J Antimicrob Chemother. Jan. 1997;39(1):5-12.*
Camilleri M, Colemont LJ, Phillips SF, Brown ML, Thomforde GM, Chapman N, Zinsmeister AR. Human gastric emptying and colonic filling of solids characterized by a new method. Am J Physiol. Aug. 1989;257(2 Pt 1):G284-90.*
Bahnmuller, Metabolites of Microorganisms. 248. Synthetic Analogs of Saphenamycin, J. Antibiot (Tokyo). Nov. 1988; 41(11): 1552-60.
Borman, Chemistry Highlights 2005, Chemical & Engineering News, Dec. 19, 2005, vol. 83, No. 51, pp. 15-20.
Cirz et al., Inhibition of Mutation and Combating the Evolution of Antibiotic Resistance, PLOS Biology, Jun. 2005, vol. 3, Issue 6, e176, pp. 1024-1033.
Darst, New Inhibitors Targeting Bacterial RNA Polymerase, TRENDS in Biochemical Sciences, vol. 29, No. 4, Apr. 2004, pp. 159-162.
Dellit, M.D., Tim, University of Washington and Infectious Diseases Society of Washington; Jeffrey Duchin, MD, Public Health-Seattle & King County and University of Washington; Jo Hofmann, MD, Washington State Department of Health and University of Washington; Erika Gurmai Olson, MD, Tacoma-Pierce County Health Department Antibiotic Resistance Task Force, Interim Guidelines for Evaluation and Management of Community-Associated Methicillin-Resistant *Staphylococcus aureus* Skin and Soft Tissue Infections in Outpatient Settings, Sep. 2, 2004.
Geiger et al., Metabolites of Microorganisms. 247. Phenazines from *Streptomyces* Antibioticus, Strain Tu 2706, J Antibiot (Tokyo). Nov. 1988;41 (11): 1542-51.
Gorwitz et al., Strategies for Clinical Management of MRSA in the Community: Summary of an Experts' Meeting Convened by the Centers for Disease Control and Prevention, Department of Health and Human Services Centers for Disease Control and Prevention, Mar. 2006.
Henry, Disabling Resistance Inhibiting Key Protease Prevents Bacteria From Evolving Drug Resistance, Chemical and Engineering News, May 16, 2005, vol. 83, No. 20, p. 8.
Johnson, N.J. Experts Urge Prudent Antibiotic Use, Examiner.Com, The Associated Press, Jul. 31, 2006.
Kitahara et al., Saphenamycin, A Novel Antibiotic From a Strain of *Streptomyces*, J Antibiot (Tokyo). Oct. 1982; 35(10):1412-4.
Laursen et al., Solid-Phase Synthesis of New Saphenamycin Analogues with Antimicrobial Activity, Bioorg. Med. Chem. Lett. Jan. 21, 2002; 12(2):171-5.
Laursen et al., First Synthesis of Racemic Saphenamycin and Its Enantiomers. Investigation of Biological Activity, Bioorg. Med. Chem. Mar. 6, 2003;11(5):723-31.
Laursen et al., Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003;1(18):3147-53.
Reusser, Inhibition of Ribosomal and RNA Polymerase Functions by Rubradirin and Its Aglycone, J Antibiot (Tokyo). Nov. 1979;32(11):1186-92.
Rihn, et al., Community-Acquired Methicillin-Resistant *Staphylococcus aureus*: An Emerging Problem in the Athletic Population, Am J Sports Med. Dec. 2005;33(12): 1924-9.
Salmenlinna et al., Community-Acquired Methicillin-Resistant *Staphylococcus aureus*, Finland, Emerg. Infect. Dis. Jun. 2002;8(6):602-7.
Salmenlinna et al., Community-Acquired Methicillin-Resistant *Staphylococcus aureus*, Finland, Emerging Infectious Diseases, vol. 8, No. 6, Jun. 2002, pp. 602-607.
Vandenesch et al., Community-Acquired Methicillin-Resistant *Staphylococcus aureus* Carrying Panton-Valentine Leukocidin Genes: Worldwide Emergence, Emerg. Infect. Dis. Aug. 2003;9(8):978-84.
Can We Prevent Bacteria From Developing Resistance to Antibiotics?, Sep. 2005, AAPS News Magazine 15.
Healthcare-Associated Methicillin Resistant *Staphylococcus aureus* (HA-MRSA), Department of Health and Human Services, Centers for Disease Control and Prevention, Jun. 1, 2005.
Methicillin-Resistant *Staphylococcus aureus*, HealthLink, Medical College of Wisconsin, Information Provided by the Wisconsin Department of Health and Family Services, Article Reviewed: Apr. 10, 2003, 2003 Medical College of Wisconsin.
Methicillin-Resistant *Staphylococcus aureus* (MRSA) Infection, Written by Dr. Alan Johnson, Clinical Scientist, Website: www.mrsasupport.co.uk, Jan. 8, 2005.
The Public's Health, Back-To-School: Review Immunization Records Early, What Doctors and Parents Need to Know About Immunizations and School, vol. 5, No. 7, Jul.-Aug. 2005.
Sulfonamide Class Antibiotics, ChemicalLand21.com.
Supplementary EP Search Report 04783885 dated Oct. 12, 2010.
Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 (Mar. 2002), 1686-1691.
Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).
Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.
Berry et al., Bacteriological Efficacies of Three Macrolides Compared with Those Amoxicillin-Clavulanate Against *Streptococcus pneumoniae* and *Haemophilus influenzae*, Antimicrob Agents Chemother. Dec. 1998; 42(12): 3193-3199.
Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.
Bhargava et al., Pulsed Feeding During Fed-Batch *Aspergillus oryzae* Fermentation Leads to Improved Oxygen Mass Transfer, Biotechnol. Prog. 2003, 19, 1091-1094.
Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, pp. 111-117.
Bishai, Comparative Effectiveness of Different Macrolides: Clarithromycin, Azithromycin, and Erythromycin, Johns Hopkins Point of Care Information Technology (POC-IT), 2004.
Bradley, *Staphylococcus aureus* Pneumonia: Emergence of MRSA in the Community, Semin Respir Crit Care Med. 2005; 26 (6): 643-649.
Brogden et al., Cefixime. A Review of Its Antibacterial Activity. Pharmacokinetic Properties and Therapeutic Potential, Drugs, Oct. 1989; 38 (4): 524-50. (Abstract).
Burgess et al., A Time-Kill Evaluation of Clarithromycin and Azithromycin Against Two Extracellular Pathogens and the Development of Resistance, The Annals of Pharmacotherapy: vol. 33, No. 12, pp. 1262-1265. (Abstract), 1999.
Byfield et al., Relevance of the Pharmacology of Oral Tegafur to its Use as a 5-FU Pro-Drug., Cancer Treat Rep. Jun. 1985; 69 (6): 645-52. (Abstract).
Cappelletty et al., Bactericidal Activities of Cefprozil, Penicillin, Cefaclor, Cefixime, and Loracarbef against Penicillin-Susceptible and -Resistant *Streptococcus pneumoniae* in an In Vitro Pharmacodynamic Infection Model, Antimicrobial Agents and Chemotherapy, May 1996, p. 1148-1152.
Cha et al., Pulsatile Delivery of Amoxicillin Against *Streptococcus pneumoniae*, Journal of Antimicrobial Chemotherapy, Advance Access Published Oct. 14, 2004.
Craig, Antibiotic Selection Factors and Description of a Hospital-Based Outpatient Antibiotic Therapy Program in the USA, Eur J Clin Microbiol Infect Dis. Jul. 1995;14(7):636-42. (Abstract).
Cremieux et al., Ceftriaxone Diffusion into Cardiac Fibrin Vegetation. Qualitative and Quantitative Evaluation by Autoradiography, Fundam Clin Pharmacol. 1991;5(1):53-60. (Abstract).

Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, p. 672-676.

Erah et al., The Stability of Amoxycillin, Clarithromycin and Metronidazole in Gastric Juice: Relevance to the Treatment of *Helicobacter pylori* Infection, J Antimicrob Chemother Jan. 1997;39(1):5-12. (Abstract).

Fang, A Study of the Ethical Considerations and Implications, Prozac Weekly and Sarafem in the Wake of Prozacs Patent Expiration, 5.22J/10.02J, Biotechnology and Engineering, 2002.

Feder et al., Once-Daily Therapy for Streptococcal pharyngitis Wtih Amoxicillin, American Academy of Pediatrics, vol. 103(1), Jan. 1999, pp. 47-51.

Freeman et al., The Cyclosporin-Erythromycin Interaction: Impaired First Pass Metabolism in the Pig, Br J Pharmacol. Jul. 1991;103(3):1709-12. (Abstract).

Frimodt-Moller, Correlation Between Pharmacokinetic / Pharmacodyamic Parameters and Efficacy for Antibiotics in the Treatment of Urinary Tract Infection, Int. J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.

Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998;42(8):1996-2001.

Gnarpe et al., Penicillin Combinations Against Multi-Resistant Urinary Pathogens as an Alternative to Gentamycin Treatment, Microbios 1976;16(65-66):201-6. (Abstract).

Gordon et al., Rationale for Single and High Dose Treatment Regimens with Azithromycin, Pediatric Infectious Disease Journal. 23(2) Supplement: S102-S107, Feb. 2004. (Abstract).

Goswick et al., Activities of Azithromycin and Amphotericin B Against *Naegleria fowleri* In Vitro and in a Mouse Model of Primary Amebic Meningoencepthalitis, Antimicrob Agents Chemother. Feb. 2003; 47(2): 524-528.

Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital, 2004.

Hickey et al., Production of Enterolysin A by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antitumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffman et al., Pharmacodynamic and Pharmacokinetic Rationales for the Development of an Oral Controlled-Release Amoxicillin Dosage Form, Journal of Controlled Release 54 (1998) 29-37.

Hoffman et al., Influence of Macrolide Susceptibility on Efficacies of Clarithromycin and Azithromycin Against *Streptococcus pneumoniae* in a Murine Lung Infection Model, Antimicrobial Agents and Chemotherapy, Feb. 2003, p. 739-746, vol. 47, No. 2.

Hyde et al., Macrolide Resistance Among Invasive *Streptococcus pneumoniae* Isolates, JAMA. Oct. 17, 2001; 286(15):1857-62. (Abstract).

Iba et al., Comparison Between Continuous Intravenous and Oral Administration of 5-FU with LV, Gan to Kagaku Ryoho. Apr. 1999; 26(5):631-5 (Abstract).

Jacobs, Pharmacodynamic Approach to Antimicrobial Treatment for Respiratory Infections, Department of Pathology, Case Western Reserve University, 2006.

Kaplan et al., Macrolide Therapy of Group A Streptococcal Pharyngitis: 10 Days of Macrolide Therapy (Clarithromycin) is More Effective in Streptococcal Eradication Than 5 Days (Azithromycin), Clin Infect Dis. Jun. 15, 2001;32(12):1798-802. Epub May 21, 2001. (Abstract).

Klugman, Bacteriological Evidence of Antibiotic Failure in Pneumococcal Lower Respiratory Tract Infections, Eur Respir J 2002; 20 Suppl. 36, 3s-8s.

Kramer et al., Statistical Optimisation of Diclofenac Sustained Release Pellets Coated with Polymethacrylic Films, Int J Pharm. Apr. 30, 2003;256(1-2):43-52. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, Oct. 2000. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.

Lamb et al., Ceftriaxone: An Update of its Use in the Management of Community-Acquired and Noscocomial Infections, Drugs. 2002;62(7):1041-89. (Abstract).

Lerner-Tung et al., Pharmacokinetics of Intrapericardial Administration of 5-Fluorouracil, Cancer Chemother Pharmacol. 1997;40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000 (Abstract).

Livermore et al., Activity of Ertapenem Against *Neisseria gonorrhoeae*, Journal of Antimicrobial Chemotherapy 2004 54(1):280-281.

Lovmar et al., Kinetics of Macrolide Action, The Josamycin and Erythromycin Cases, J. Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Administration, Journal of Antimicrobial Chemotherapy (2002) 50, 699-706.

Marten et al., Monthly Report, Jul. 2004, Pulsatile Dosing of Antifungal Compounds, UMBC; to Dr. Robert J. Guttendorf, Advancis Pharmaceutical Corp.

Marten et al., Monthly Report, Aug. 2004, Pulsatile Dosing of Antifungal Compounds, UMBC; to Dr. Robert J.Guttendorf, Advancis Pharmaceutical Corp.

Mazzei et al., How Macrolide Pharmacodynamics Affect Bacterial Killing, Infect Med 16(sE):22-28, 1999. (Abstract).

Nightingale, Pharmacokinetics and Pharmacodynamics of Newer Macrolides, Pediatric Infectious Disease Journal. 16(4):438-443, Apr. 1997. (Abstract).

Olofinlade et al. Anal Carcinoma: A 15-Year Retrospective Analysis, Scand J Gastroenterol 2000:35;1194-1199.

Pacifico et al., Comparative Efficacy and Safety of 3-Day Azithromycin and 10-Day Penicillin V Treatment of Group A Beta-Hemolytic Streptococcal Pharyngitis in Children, Antimicroial Agents and Chemotherapy, Apr. 1996, 1005-1008, vol. 40, No. 4. (Abstract).

Parmar-Lapasia et al., A Comparison of Two Macrolide Antibiotics in the Treatment of Community-Acquired Infections, P & T (Pharmacy & Therapeutics), Oct. 2003, vol. 28, No. 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15, 2001): 4267-4269.

Polak, Pharmacokinetics of Amphotericin B and Flucytosine, Postgrad Med J. Sep. 1979;55(647):667-70. (Abstract).

Porter et al., Antibiotics and Infectious Diseases in Otolaryngology—HNS, Grand Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.
Ranga Rao et al., Influence of Molecular Size and Water Solubility of the Solute on its Release from Swelling and Erosion Controlled Polymeric Matrices, Journal of Controlled Release, 12 (1990) 133-141.
Reza et al., Comparative Evaluation of Plastic, Hydrophobic and Hydrophilic Polymers as Matrices for Controlled-Release Drug Delivery, J. Pharm Pharmaceut Sci, 6(2):282-291, 2003.
Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5):909-10 (Abstract).
Rivkees et al., Dexamethasone Treatment of Virilizing Congenital Adrenal Hyperplasia: The Ability to Achieve Normal Growth, Pediatrics 2000; 106; 767-773.
Roblin et al., In Vitro Activity of a New Ketolide Antibiotic, HMR 3647, Against *Chlamydia pneumoniae*, Antimicrob Agents Chemother. Jun. 1998; 42(6): 1515-1516.
Santini et al., The Potential of Amifostine: From Cytoprotectant to Therapeutic Agent, Haematologica Nov. 1999; 84(ii): 1035-1042.
Sanz et al., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.
Schaad et al., Azithromycin Versus Penicillin V for Treatment of Acute Group A Streptococcal Pharyngitis, The Pediatric Infectious Disease Journal: vol. 21(4) Apr. 2002 pp. 304-308.
Schweizer et al., "Single Shot" Prevention in Abdominal Surgery. Antibiotics with Long Half-Life (Cefriaxone, Omidazole) vs. Antibiotics with Short Half-Life (Cefazolin, Metronidazole, Clindamycin), Helv Chir Acta. Apr. 1994;60(4):483-8. (Abstract).
Shvartzman et al., Treatment of Streptococcal Pharyngitis with Amoxycillin Once a Day, BMJ vol. 306, pp. 1170-1172, May 1, 1993.
Stringer et al., Section 3: Diseases of the Ear, Part 4: Inner Ear, Chapter 46: Ototoxicity, Paparella: vol. II, Otology and Neuro-Otology, 1990.
Suda et al., The Synthesis and In Vitro and In Vivo Stability of 5-Fluorouracil Prodrugs Which Possess Serum Albumin binding Potency, Biol Pharm Bull. Sep. 1993;16(9):876-8. (Abstract).
Sandip et al., Controlled Release Formulation of Tramadol Hydrochloride Using Hydrophilic and Hydrophobic Matrix System, AAPS PharmSciTech 2003; 4 (3) Article 31.
Todar's Online Textbook of Bacteriology, Antimicrobial Agents Used in Treatment of Infectious Disease, 2002 Kenneth Todar University of Wisconsin-Madison Department of Bacteriology.
Vanderkooi et al., Antimicrobial Resistance and the *Pneumococcus*, Infectious Diseases and Microbiology, vol. 3, Issue 5, May 2004.
Villalobos et al., Pharmacokinetics and Pharmacodynamics of Antibacterial Agents in Pediatrics: A Practical Approach, Jacksonville Medicine, Aug. 1998.
Waters, Colorectal Cancer-Drug Treatment, Hospital Pharmacist, vol. 11, pp. 179-192, May 2004.
Wattenberg, Prevention of Carcinogenesis of the Respiratory Tract by Chemopreventive Agents Delivered by Aerosol, International Society of Cancer Chemoprevention, vol. 1, No. 5, Jan. 2003.
Whitehead et al., Amoxycillin Release From a Floating Dosage Form Based on Alginates, International Journal of Pharmaceutics 210 (2000) 45-49.
Yousef et al., Combined Action of Amoxycillin and Dicloxacillin Against *Staphylococcus aureus* In Vitro, Pharmazie Sep. 1985; 40(9):650-1. (Abstract).
About Macrolides, About That Bug.com, 2006.
Acepromazine Maleate, DRUGS, 2004.
Allergy Site Navigator, Drug Classification A-D, 2004.
Amoxycillin (As Trihydrate), Moxyvit, 2003.
Amoxicillin + Clavulanate, PetPlace.com, 2006.
Answers.com, Macrolide, 2006.
Antimetabolites, GPnotebook, 2005.
Augmentin, Product Information, GlaxoSmithKline, Physicians Desk References, pp. 1421-1433, 2004.
Augmentin XR (PDR entry for) (GlaxoSmithKline), (Amoxicillin/Clavulanate Potassium), Extended Release Tablets, Jun. 2004.
Beta Lactam Antibiotics, Health 24.com, 2005.
Biaxin XL, Once-Daily Biaxin XL Clarithromycin Extended-Release Tablets, Abbott Laboratories Online, 2004.
Biaxin XL Once-daily, Abbott, 2006.
Biaxin, Dosage and Administration, 2006.
Biaxin Filmtab, Biaxin XL Filmtab, Biaxin Granules, pp. 1-25, Abbott Laboratories, 2005.
Body Chemistry, Acid Alkaline Foods, Acid Reflux? Gas, Acid Indigestion, Acid/Alkaline Balance, 2005.
Carers of Crohns, Antibiotics, 2006.
Citizen Petition, McNeil Consumer & Specialty Pharmaceuticals, Mar. 19, 2004.
Clarithromycin Extended-Release Scientific Posters Presented to the 39th Interscience Conference on Antimicrobial Agents and Chemotherapy (ICAAC), San Francisco, Sep. 26-29, 1999.
Clearance and the Elimination Rate Constant, Ke (Elimination Rate)—Half-Life, Oct. 14, 2002.
Complementary Medicine Saves Money, Medicine, Greenhealthwatch.com, 2002.
Cross-Reference Art Collections, 901-907; USPTO.gov, 2004.
Declaration of Michael J. Rybak. from the prosecution history of U.S. Appl. No. 09/792,092, filed Sep. 23, 2002.
Dispensing Errors With Depakote, New Formulation Creates Confusion, Patient Safety, Practitioners Reporting News, USP Issued Mar. 3, 2001.
Drugs.com, Drug Information for Diclofenac (Topical), 2006.
Drug, Bio-Affecting and Body Treating Compositions (Class 424), 475 Sustained or differential release, United States Patent and Trademark Office, 2006.
Elimination Rate Constant/Half-Life, Ke (Elimination Rate)—Half-Life, Oct. 14, 2002.
Emulsions, 2006.
Encyclopedia Britannica Online, Types of Drugs>Antimicrobial Drugs>Antibiotics>Macrolides, 2006.
Excenel, Swine Health Management, Prewean Program. Pfizer Salud Animal, 2005.
Fabrication of Metronidazole Strips, 996 Die Pharmazie 50(Feb. 1995) No. 2.
Five vs. 10 Days of Therapy for Streptococcal Pharyngitis, American Family Physician, Feb. 15, 2001.
Food and Drug Administration Center for Drug Evaluation and Research Approved Drug Products With Therapetutic Equivalence Evaluations, 24th Edition, 2004.
Getting a Drug Into the Body: Absorption, 2005.
Highlights on Antineoplastic Drugs, Pharmacia, vol. 11. No. 4, 1993.
Jock Itch and Other dermatophytes . . . , Mycolog, 2002.
Klarithran, Ranbaxy(SA)(PTY) LTD, Jun. 2005.
Klucel Hydroxypropylcellulose (HPC). Hercules Incorporated, 2004.
MedicineNet.com, Generic Name: Acyclovir, Brand Name: Zovirax, Dec. 31, 1997.
Meeting the Challenge of a New Generation of Respiratory Pathogens, MAC, 2001.
The Merck Index, An Encyclopedia of Chemicals, Drugs, and Biologicals, Twelfth Edition, pp. 397-398, 1996.
Methods of Formulating Controlled Release Products Outside of the Claims of Forest Laboratory Patents U.S. 4,369,172 and U.S. 4,389,393, Technical Information, Dow Chemical, Feb. 1991.
Miconazole, The Merck Index Results-Form View, Monograph No. 06202, 2005.
Mode of Action of Macrolides in Blocking Translation During Bacterial Protein Synthesis: Blocking Peptidyltransferase. Doc Kaiser's Microbiology Home Page, Oct. 13, 2004.
Module 8—Therapeutics. May 25, 2002, Newcastle., BPAIIG Immunology/Infectious Diseases Training Programme, Module: Therapeutics, 2002.
Monistat, Which Treatment is Right for You?, Vaginal vs. Oral Therapy, 2004.
*Neisseria meningitidis*, The Doctor's Doctor, Nov. 8, 2004.

New-Generation Aromatase Inhibitor for Breast Cancer: Anastrozole Challenges Tamoxifen in First-Line Therapy, 10th European Cancer Conference (ECCO 10), Vienna, Austria/ Sep. 12-16, 1999.

New Product Newswire, Drug Topics Archive, Aug. 5, 2002.

Nitrofurantoin, Eckerd Prescription Advisor, Feb. 15, 2001.

Nursing, Cancer Nursing: Principles and Practice, Fifth Edition, Jones and Bartlett Publishers, 2000.

Oral Capecitabine Should Improve Convenience of Chemoradiation for Locally Advanced Rectal Cancer—New Treatment Appears to be Safe and Effective, PeerView Press, Chemotherapy (ICAAC), Sep. 27-30, 2002; San Diego, CA., 40th Annual Meeting of Infectious Diseases Society.

Oral Extended (Controlled) Release Dosage Forms, In Vivo Bioequivalence and In Vitro Dissolution Testing, Office of Generic Drugs, 1993.

Pharmaceuticals, Pharmacos Unit F2 Pharmaceuticals V 6.0, Eudralex Collection 3AQ19a 1992.

Physicians Desk Reference, PDR 57 Edition 2003, p. 402/Abbott.

Principles of Diagnosis of Infectious Diseases and Antimicrobial Therapy, Chapter 1, 2004.

Procardia XL (Nifedipine) Extended Release Tablets for Oral Use, 69-4467-00-8, Pfizer Labs, Aug. 2003.

Summary of Product Characteristics, Doxycycline Capsules BP 50mg, 2001.

Sustained or Differential Release Type, USPTO Classification Definitions (Dec. 2002 Edition) 964, 2006.

Sustained-Release Dosage Forms, Degussa, Rohm Pharma Polymers, 2006.

Testicular Cancer: Questions and Answers, Cancer Facts, National Cancer Institute, Aug. 14, 2003.

Traditional Chemotherapy, Chapter 25 from Prevention and Therapy of Cancer and Other Common Disease: Alternative and Traditional Approaches; Infomedix 1996.

\* cited by examiner

ANTIBIOTIC PRODUCT, USE AND FORMULATION THEREOF

This application claims the priority of U.S. Provisional Application Ser. No. 60/503,041 filed on Sep. 15, 2003, the disclosures of which are hereby incorporated by reference in their entireties.

This invention relates to an antibiotic product, as well as the use and formulation thereof.

A wide variety of antibiotics have been used, and will be used, in order to combat bacterial infection. In general, such antibiotics can be administered by a repeated dosing of immediate release dosage forms, which results in poor compliance or as a controlled release formulation (slow release) at higher administered doses. The present invention is directed to providing for an improved antibiotic product.

In accordance with one aspect of the present invention, there is provided an antibiotic pharmaceutical product which is comprised of at least two, preferably at least three, antibiotic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the first and second dosage forms each start release of the antibiotic contained therein at about the same time, and the third dosage form starts release of the antibiotic contained therein at a time after the second dosage form starts release of antibiotic contained therein.

In another particularly preferred embodiment, there are at least two, preferably at least three dosage forms, each of which has a different release profile and the release profile of each of the dosage forms is such that the dosage forms each start release of the antibiotic contained therein at different times after administration of the antibiotic product.

Thus, in accordance with an aspect of the present invention, there is provided a single or unitary antibiotic product that has contained therein at least two, preferably at least three antibiotic dosage forms, each of which has a different release profile, whereby the antibiotic contained in at least two of such dosage forms is released at different times.

In general neither of the second or third dosage forms starts release of antibiotic contained therein before the first dosage form starts release of antibiotic contained therein.

More particularly, in one aspect, the antibiotic product contains at least three dosage forms, the first of which is a delayed release dosage form, the second of which is a delayed release dosage form, and the third of which is a delayed sustained release dosage form, with the third dosage form initiating release at about the same time as the second dosage form or at a time after the second dosage form (the initiation of sustained release is delayed for a period of time after initiation of release from the second dosage form), with the third dosage form initiating release after release is initiated from both the first and second dosage forms.

In accordance with a further aspect of the invention, the antibiotic product may be comprised of at least four different dosage forms, at least three of which starts to release the antibiotic contained therein at different times after administration of the antibiotic product.

The antibiotic product generally does not include more than five dosage forms with different release times.

In accordance with a preferred embodiment, the antibiotic product has an overall release profile such that when administered the maximum serum concentration of the total antibiotic released from the product is reached in less than twelve hours after initiation of release of antibiotic from the first dosage form, preferably in less than eleven hours after initiation of release of antibiotic from the first dosage form. In an embodiment, the maximum serum concentration of the total antibiotic released from the antibiotic product is achieved no earlier than four hours after initiation of release of antibioitic from the first dosage form.

In accordance with one preferred embodiment of the invention, there are at least three dosage forms. The first and second of the at least three dosage forms are delayed release dosage forms whereby initiation of release of the antibiotic therefrom is delayed after administration of the antibiotic product. The third of the at least three dosage forms is a delayed sustained release dosage form. Additionally, initiation of release of the antibiotic from the third delayed sustained release dosage form is delayed until after initiation of release from the second, however, when release is initiated the third dosage form releases antibioitc as a sustained release dosage form. The delay of initiation of release from the sustained release dosage form, may be accomplished for example by using a pH sensitive or a non-pH sensitive enteric coating, depending on the type of antibiotic product, whereby the sustained release of the antibiotic from the third dosage form is delayed with the third dosage form initiating release at about the same time or at a time after initiation of release of antibiotic from the second dosage form. More particularly, the antibiotic released from the second of the at least three dosage forms achieves a $C_{max}$ (maximum serum concentration in the serum) at a time after the antibiotic released from the first of the at least three dosage forms achieves a $C_{max}$ in the serum, and the antibiotic released from the third dosage form achieves a $C_{max}$ in the serum after the $C_{max}$ of antibiotic released from the second dosage form.

In one embodiment the first and second of the at least two dosage forms initiate delayed release of antibiotic at about the same time.

In one embodiment the initiation of the delayed release of antibiotic from the second of the at least two dosage forms is delayed until after the initiation of release of antibiotic from the first dosage form.

In all embodiments comprising three or more dosage forms, the initiation of the delayed release of antibiotic from the second dosage form is delayed until after the delayed release of antibiotic is initiated from the first dosage form.

In one embodiment, the second of the at least two dosage forms initiates release of the antibiotic contained therein at least one hour after the first dosage form, with the initiation of the release therefrom generally occurring no more than six hours after initiation of release of antibiotic from the first dosage form of the at least three dosage forms.

In general, the first dosage form produces a $C_{max}$ for the antibiotic released therefrom within from about 0.5 to about 2 hours after initiation of release of antibiotic, with the second dosage form of the at least three dosage forms producing a $C_{max}$ for the antibiotic released therefrom in no more than about four hours after initiation of release of antibiotic from the first dosage form. In general, the $C_{max}$ for such second dosage form is achieved no earlier than two hours after initiation of release of antibiotic from the first dosage form; however, it is possible within the scope of the invention to achieve $C_{max}$ in a shorter period of time.

As hereinabove indicated, the antibiotic product may contain at least three or at least four or more different dosage forms. For example, if the antibiotic product includes a third dosage form, the antibiotic released therefrom reaches a $C_{max}$ at a time later than the $C_{max}$ is achieved for the antibiotic released from each of the first and second dosage forms. In a preferred embodiment, release of antibiotic from the third dosage form is started after initiation of release of antibiotic from both the first dosage form and the second dosage form. In one embodiment, $C_{max}$ for antibiotic released from the third dosage form is achieved within eight hours after initiation of release of antibiotic from the first dosage form.

In another embodiment, the antibiotic product contains at least four dosage forms, with each of the at least four dosage forms having different release profiles, whereby the antibiotic released from each of the at least four different dosage forms achieves a $C_{max}$ at a different time.

As hereinabove indicated, in a preferred embodiment, irrespective of whether the antibiotic contains at least two or at least three or at least four different dosage forms each with a different release profile, $C_{max}$ for all the antibiotic released from the antibiotic product is achieved in less than twelve hours after initiation of release of antibiotic from the first is initiated, and more generally is achieved in less than eleven hours after initiation of release of antibiotic from the first is initiated.

In a preferred embodiment, the antibiotic product is a once a day product, whereby after administration of the antibiotic product, no further product is administered during the day; i.e., the preferred regimen is that the product is administered only once over a twenty-four hour period. Thus, in accordance with the present invention, there is a single administration of an antibiotic product with the antibiotic being released in a manner such that overall antibiotic release is effected with different release profiles in a manner such that the overall $C_{max}$ for the antibiotic product is reached in less than twelve hours after initiation of release of antibiotic. The term single administration means that the total antibiotic administered over a twenty-four hour period is administered at the same time, which can be a single tablet or capsule or two or more thereof, provided that they are administered at essentially the same time.

Applicant has found that a single dosage antibiotic product comprised of at least three antibiotic dosage forms each having a different release profile is an improvement over a single dosage antibiotic product comprised of an antibiotic dosage form having a single release profile. Each of the dosage forms of antibiotic in a pharmaceutically acceptable carrier may have one or more antibiotics and each of the dosage forms may have the same antibiotic or different antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

If at least four dosage forms are used, the fourth of the at least four dosage forms may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antibiotic release from such fourth dosage form may be initiated prior to or after release from the second or third dosage form.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the delayed release dosage forms are in the continuous phase, and the delayed sustained release dosage form is in a discontinuous phase. The formulation may also be produced in a manner for delivery of three dosage forms as hereinabove described. For example, there may be provided an oil-in-water-in-oil emulsion, with oil being a continuous phase that contains the third delayed sustained release component, water dispersed in the oil containing a first delayed release dosage form, and oil dispersed in the water containing a second delayed release dosage form.

It is also within the scope of the invention to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic product with at least three different dosage forms with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is a delayed sustained release tablet, and may also include two or more additional tablets, each of which provides for a delayed release of the antibiotic, as hereinabove described, whereby the $C_{max}$ of the antibiotic released from each of the tablets is reached at different times, with the $C_{max}$ of the total antibiotic released from the antibiotic product being achieved in less than twelve hours after initial release of antibiotic.

The formulation of an antibiotic product including at least three dosage forms with different release profiles for different routes of administration is deemed to be within the skill of the art from the teachings herein. As known in the art, with respect to sustained release, the time of release can be controlled by the concentration of antibiotics in the coating and/or the thickness of the coating.

In accordance with the present invention, each of the dosage forms contains the same antibiotic; however, each of the dosage forms may contain more than one antibiotic.

Immediate Release Component

An immediate release component may be initially produced and then coated to produce the delayed release dosage forms used in the present invention.

An immediate release component is used in formulating the delayed release dosage form and can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such as low molecular weight PEGs (PEG2000-10000) and high molecular weight PEGs (Polyox) with molecular weights above 20,000 daltons.

It may be useful to have these materials present in the range of 1.0 to 60% (W/W). More preferably these materials are present in the range of 3-40%. Most preferably these materials are present in the range of 5-20% so that the drug loading may be kept high and the overall dosage form size is minimized.

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monostearate, polyoxyethylene sorbitan monooleate, glyceryl monostearate, glyceryl monooleate, glyceryl monobutyrate, caprylocaproyl macrogol-8-glycerides, one of the non-ionic surfactants such as the Pluronic line of surfactants, or any other material with surface active properties, or any combination of the above. The material may also be a disentegrant or superdisentegrant known to those in the art such as coscarmellose sodium, cross linked PVP, and others.

These materials may be present in the rate of 0.05-15% (W/W).

The Non-pH Sensitive Delayed Release Component

The components in this composition are the same as the immediate release unit, but with additional polymers integrated into the composition, or as coatings over the pellet or granule. Several methods to affect a delayed release with non pH dependent polymers are known to those skilled in the art. These include soluble or erodible barrier systems, enzymatically degraded barrier systems, rupturable coating systems, and plugged capsule systems among others. These systems have been thoroughly described in the literature (see "A Review of Pulsatile Drug Delivery" by Bussemer and Bodmeier in the Winter 2001 issue of American Pharmaceutical Review) and formulations and methods for their manufacture are hereby incorporated by reference.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit RS) cellulose acetate, and ethylcellulose.

Typically these materials can be present in the range of 0.5-25% (W/W) of this component. Preferably the materials are present in an amount just enough to provide the desired in vivo lag time and $T_{max}$.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (W/W) or more. Preferably the materials are present in an amount just enough to provide the desired in vivo lag time and $T_{max}$.

Sustained Release Component

The components in this composition are the same as the immediate release component, but with additional polymers integrated into the composition, or as coatings over the pellet or granule.

The kind of materials useful for this purpose can be, but are not limited to, ethylcellulose,hydroxypropylmethylcellulose, hydroxypropylcellulose, hydroxyethylcellulose, carboxymethylcellulose, methylcellulose, nitrocellulose, Eudragit RS, and Eudragit RL, Carbopol, or polyethylene glycols with molecular weights in excess of 8,000 daltons.

These materials can be present in concentrations from 4-20% (W/W). Preferably the amounts are just enough to provide the desired in vivo release profile.

When it is desired to delay inititiation of release of the sustained release dosage form, an appropriate coating may be used to delay inititiation of the sustained release, such as a pH sensitive or a non-pH sensitive coating.

The Non-pH Sensitive Coating for Sustained Release Dosage Form

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit RS), cellulose acetate, and ethylcellulose.

Typically these materials can be present in the range of 0.5-25% (W/W) of this component. Preferably the materials are present in an amount just enough to provide the desired in vivo lag time and $T_{max}$.

The pH Sensitive Coating for Sustained Release Dosage Form

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (WIW) or more. Preferably the materials are present in an amount just enough to provide the desired in vivo lag time and $T_{max}$.

As hereinabove indicated, the units comprising the antibiotic composition of the present invention can be in the form of discrete pellets or particles contained in the capsule, or particles embedded in a tablet or suspended in a liquid suspension.

The antibiotic composition of the present invention may be administered, for example, by any of the following routes of administration: sublingual, transmucosal, transdermal, parenteral, etc., and preferably is administered orally. The composition includes a therapeutically effective amount of the antibiotic, which amount will vary with the antibiotic to be used, the disease or infection to be treated, and the number of times that the composition is to be delivered in a day. The composition is administered to a host in an amount effective for treating a bacterial infection.

This system will be especially useful in extending the practial therapeutic activity for antibiotics with elimination half lives of less than 20 hours and more particularly with elimination half-lives of less than 12 hours, and will be particularly useful for those drugs with half-lives of 2-10 hours: The following are examples of some antibiotics with half-lives of about 1 to 12 hours: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefinetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, peniciliin V, peniciliin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, suflamerazine, sulfamethazine, sulfamethixole, sulfasalazine, sulfisoxazole, sulfapyrizine, sulfadiazine, sulfinethoxazole, sulfapyridine, metronidazole, methenamine, fosfomycin, nitrofurantoin, trimethoprim, clofazimine, co-triamoxazole, pentamidine, and trimetrexate.

The invention will be further described with respect to the following examples; however, the scope of the invention is not limited thereby. All percentages in this specification, unless otherwise specified, are by weight.

EXAMPLES

I. Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum over or forced-air oven. The product may be sieved or granulated, and compressed using a suitable tablet press, such as a rotary tablet press, or filled into a capsule or sachet with a suitable filler.

Example 1

| Ingredient | Conc. (% W/W) |
| --- | --- |
| Amoxicillin | 65% (W/W) |
| Microcrystalline cellulose | 20 |
| Povidone | 10 |
| Croscarmellose sodium | 5 |

Example 2

| Amoxicillin | 55% (W/W) |
| --- | --- |
| Microcrystalline cellulose | 25 |
| Povidone | 10 |
| Croscarmellose sodium | 10 |

Example 3

| Amoxicillin | 65% (W/W) |
| --- | --- |
| Microcrystalline cellulose | 20 |
| Hydroxypropylcellulose | 10 |

Example 4

| Croscarmellose sodium | 5 |
| --- | --- |
| Amoxicillin | 75% (W/W) |
| Polyethylene glycol 4000 | 10 |
| Polyethylene glycol 2000 | 10 |
| Hydroxypropylcellulose | 5 |

Example 5

| Amoxicillin | 75% (W/W) |
| --- | --- |
| Polyethylene glycol 8000 | 20 |
| Polyvinylpyrrolidone | 5 |

Example 6

| Clarithromycin | 65% (W/W) |
| --- | --- |
| Microcrystalline cellulose | 20 |
| Hydroxypropylcellulose | 10 |
| Croscarmellose sodium | 5 |

Example 7

| Clarithromycin | 75% (W/W) |
| --- | --- |
| Microcrystalline cellulose | 15 |
| Hydroxypropylcellulose | 5 |
| Croscarmellose sodium | 5 |

Example 8

| | |
|---|---|
| Clarithromycin | 75% (W/W) |
| Polyethylene glycol 4000 | 10 |
| Polyethylene glycol 2000 | 10 |
| Hydroxypropylcellulose | 5 |

Example 9

| | |
|---|---|
| Clarithromycin | 75% (W/W) |
| Polyethylene glycol 8000 | 20 |
| Polyvinylpyrrolidone | 5 |

Example 10

| | |
|---|---|
| Ciprofloxacin | 65% (W/W) |
| Microcrystalline cellulose | 20 |
| Hydroxypropylcellulose | 10 |
| Croscarmellose sodium | 5 |

Example 11

| | |
|---|---|
| Ciprofloxacin | 75% (W/W) |
| Microcrystalline cellulose | 15 |
| Hydroxypropylcellulose | 5 |
| Croscarmellose sodium | 5 |

Example 12

| | |
|---|---|
| Ciprofloxacin | 75% (W/W) |
| Polyethylene glycol 4000 | 10 |
| Polytheylene glycol 2000 | 10 |
| Hydroxypropylcellulose | 5 |

Example 13

| | |
|---|---|
| Cirpofloxacin | 75% (W/W) |
| Polyethylene glycol 8000 | 20 |
| Polyvinylpyrrolidone | 5 |

Example 14

| | |
|---|---|
| Ceftibuten | 75% (W/W) |
| Polyethylene glycol 4000 | 10 |
| Polyethylene glycol 2000 | 10 |
| Hydroxypropylcellulose | 5 |

Example 15

| | |
|---|---|
| Ceftibuten | 75% (W/W) |
| Polyethylene Glycol 4000 | 20 |
| Polyvinylpyrrolidone | 5 |

II. Non-pH Sensitive Delayed Release Component

Any of the methods described in "A Review of Pulsatile Drug Delivery" by Bussemer and Bodmeier in the Winter 2001 issue of American Pharmaceutical Review may be utilized to make the pH independent delayed release component described. Examples 16 and 17 utilize an organic acid layer underneath a layer of Eudragit RS to result in a rapid increase in the permeability of the Eudragit film after a set amount of time depending on the permeability and thickness of the film thus allowing the inner core to release through the Eudragit membrane. Example 18 utilizes a core with a highly swellable polymer that ruptures the insoluble coating membrane after a certain amount of time determined by the permeability, plasticity and thickness of the external cellulose acetate membrane. The coatings are applied to the core via methods such as wurster column coating in a fluid bed processor as known to those skilled in the art.

Additionally, this component may be formed as in example 19. In this example the component is prepared by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven.

After the component is allowed to cool, the product may be sieved or granulated, and compressed using a suitable tablet press, such as a rotary tablet press, or filled into a capsule with a suitable encapsulator.

Example 16

| Ingredient | Conc. (% W/W) |
|---|---|
| Core from Example 4 | 65% (W/W) |
| Citric Acid | 10 |
| Eudragit RS Polymer | 20 |
| Talc | 4 |
| TEC | 1 |

Example 17

| | |
|---|---|
| Core from Example 9 | 75% (W/W) |
| Citric Acid | 10 |
| Eudragit RS Polymer | 10 |
| Talc | 4 |
| TEC | 1 |

Example 18

| | |
|---|---|
| Core from Example 1 | 93% (W/W) |
| Cellulose Acetate | 6.75 |
| PEG 400 | 0.25 |

Example 19

| | |
|---|---|
| Ciprofloxacin | 70% (W/W) |
| Polyox | 20 |
| Hydroxypropylcellulose | 5 |
| Croscarmellose sodium | 5 |

III. Enteric Delayed Release Component

Examples 20-27 utilize film coating techniques commonly known to those skilled in the art to create the enteric release component by layering of such enteric polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary.

To create a matrix type enteric component, formulate the ingredients of examples 28-32 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

Example 20

| Ingredient | Conc. (% W/W) |
|---|---|
| Core from Example 1 | 65% (W/W) |
| Cellulose Acetate Pthalate | 30 |
| TEC | 5 |

Example 21

| | |
|---|---|
| Core from Example 5 | 75% (W/W) |
| Cellulose Acetate Pthalate | 20 |
| Triacetin | 5 |

Example 22

| | |
|---|---|
| Core from Example 1 | 65% (W/W) |
| Eudragil L | 25 |
| Talc | 8 |
| TEC | 2 |

Example 23

| | |
|---|---|
| Core from Example 1 | 65% (W/W) |
| Eudragit FS | 28 |
| Talc | 5 |
| TEC | 2 |

Example 24

| | |
|---|---|
| Core from Example 1 | 65% (W/W) |
| Eudragit S | 28 |
| Talc | 5 |
| TEC | 2 |

Example 25

| | |
|---|---|
| Core from Example 7 | 75% (W/W) |
| Eudragit L | 20 |
| Talc | 3.5 |
| TEC | 1.5 |

Example 26

| | |
|---|---|
| Core from Example 11 | 60% (W/W) |
| Eudragit L | 35 |
| Talc | 4 |

Example 27

| | |
|---|---|
| Core from Example 15 | 65% (W/W) |
| Cellulose Acetate Pthalate | 32.5 |
| TEC | 2.5 |

Example 28

| | |
|---|---|
| Amoxicillin | 75% (W/W) |
| Microcrystalline Cellulose | 5 |
| Hydroxypropylcellulose pthalate | 20 |

Example 29

| | |
|---|---|
| Amoxicillin | 60% (W/W) |
| Lactose | 10 |
| Eudgragit L 30D | 30 |

Example 30

| | |
|---|---|
| Ciprofloxacin | 70% (W/W) |
| Polyethylene glycol 4000 | 10 |
| Cellulose acetate pthalate | 20 |

Example 31

| | |
|---|---|
| Clarithromycin | 60% (W/W) |
| Polyethylene glycol 2000 | 10 |
| Lactose | 20 |
| Eudgragit L 30D | 10 |

Example 32

| | |
|---|---|
| Ceftibuten | 70% (W/W) |
| Microcrystalline cellulose | 20 |
| Cellulose acetate pthalate | 10 |

IV. Sustained Release Component

Examples 33-38 utilize film coating techniques commonly known to those skilled in the art to create the sustained release component by layering of such sustained release polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary. Curing studies are recommended with sustained release membranes.

To create a matrix type sustained release component, formulate the ingredients of example 39-42 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

Example 33

| Ingredient | Conc. (% W/W) |
|---|---|
| Core from Example 1 | 75% (W/W) |
| Ethylcellulose | 20 |
| HPC | 5 |

Example 34

| | |
|---|---|
| Core from Example 5 | 80% (W/W) |
| Eudragit RS | 10 |
| Eudragit RL | 5 |
| Talc | 3 |
| TEC | 2 |

Example 35

| | |
|---|---|
| Core from Example 5 | 90% (W/W) |
| Ethylcellulose | 9 |
| Triacetin | 1 |

Example 36

| | |
|---|---|
| Core from Example 7 | 90% (W/W) |
| Surelease | 10 |

Example 37

| | |
|---|---|
| Core from Example 11 | 85% (W/W) |
| Kollicoat SR | 10 |
| TBC | 5 |

Example 38

| | |
|---|---|
| Core from Example 15 | 80% (W/W) |
| Polyethylene glycol 8000 | 5 |
| Eudragit RS 30D | 15 |

Example 39

| | |
|---|---|
| Amoxicillin | 75% (W/W) |
| Hydroxyethylcellulose | 10 |
| Polyethylene glycol 4000 | 10 |
| Hydroxypropylcellulose | 5 |

Example 40

| | |
|---|---|
| Ciprofloxacin | 75% (W/W) |
| Lactose | 10 |
| Povidone (PVP) | 10 |
| Polyethylene glycol 2000 | 5 |

Example 41

| | |
|---|---|
| Clarithromycin | 75% (W/W) |
| Polyethylene glycol 4000 | 10 |
| Povidone (PVP) | 10 |
| Hydroxypropylcellulose | 5 |

Example 42

| | |
|---|---|
| Ceftibuten | 75% (W/W) |
| Lactose | 15 |
| Polyethylene glycol 4000 | 5 |
| Polyvinylpyrrolidone | 5 |

V. Sustained Release Dosage form with Coating to Delay Initiation of Sustained Release:

Delaying the initiation of the sustained release of antibiotic in the present invention is achieved by either coating the immediate release component bead with a sustained release coating and then subsequently applying an enteric coating or non- pH sensitive delayed release coating to that coated bead, or alternatively the sustained release matrix component bead may be coated with an enteric coating or non-pH sensitive delayed release coating.

Coatings can be applied to either the sustained release coated beads or the sustained release matrix beads to form a product which pulses the therapeutic agent in a desired environment or location of the GI tract.

V A. The following examples describe the detailed preparation of the sustained-release coating materials to be applied to the immediate release beads from section I of the examples, resulting in a sustained release component of the invention.

Example 43

Eudragit RS Example—Organic Coating

| Component | Percentage (%) |
|---|---|
| Part A | |
| Eudragit RS-100 | 6.0 |
| Triethyl Citrate | 1.0 |
| Talc | 0.5 |
| Acetone | 92.5 |

Step 1. Dissolve Eudragit in Acetone.

Step 2. Mix TEC and talc in a separate container with some Acetone.

Step 3. Add step 2 to Step 1, and allow to mix for 20 minutes before spraying.

Example 44. Surelease™ Example—Aqueous Coating

| Component | Percentage (%) |
|---|---|
| Part A | |
| Surelease | 90 |
| Purified Water | 10.0 |

Step 1. Mix surelease and water for 30 minutes before spraying.

Directions for application of the sustained release coating to the beads:

Charge a wurster column equipped fluid bed with the beads to be coated. Spray the coating onto the beads at a rate and temperature known to those skilled in the art of bead coating so as to efficiently coat the beads to give a weight gain of between 4 and 20%. Dry the beads to the specified level of coating solvent for optimum handling and stability. Cure the beads for additional congealing of the sustained release film if required.

V B. The following are examples of the pH sensitive, or enteric release, coating that can be used to optionally delay the onset of action of any or all of the second, third, or additional dosage forms.

The composition of the aqueous Eudragit L30D-55 dispersion to be applied to the immediate release components that have been treated with the above-described sustained release coatings, or to the sustained-matrix pellets is provided below in Example 45.

Example 45

Eudragit® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

Preparation Procedure for an Eudragit® L 30 D-55 Aqueous Dispersion
Step 1 Suspend triethyl citrate and talc in deionized water.
Step 2 The TEC/talc suspension is then homogenized using a PowerGen 700 high shear mixer.
Step 3 Add the TEC/talc suspension slowly to the Eudragit® L 30 D-55 latex dispersion while stirring.
Step 4 Allow the coating dispersion to stir for one hour prior to application onto the matrix pellets.

Example 46

Preparation of an Eudragit® S 100 Aqueous Coating Dispersion Dispersion Formulation The composition of the aqueous Eudragit® S 100 dispersion applied to the matrix pellets is provided below:
Eudragit® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

Preparation Procedure for an Eudragit® S 100 Aqueous Dispersion
Part I:
(i) Dispense Eudragit® S 100 powder in deionized water with stirring.
(ii) Add ammonium hydroxide solution drop-wise into the dispersion with stirring.
(iii) Allow the partially neutralized dispersion to stir for 60 minutes.
1(iv) Add triethyl citrate drop-wise into the dispersion with stirring. Stir for about 2 hours prior to the addition of Part B.
Part II:
(i) Disperse talc in the required amount of water
(ii) Homogenize the dispersion using a PowerGen 700D high shear mixer.
(iii) Part B is then added slowly to the polymer dispersion in Part A with a mild stirring.

Coating Conditions for the Application of Aqueous Coating Dispersions

The following coating parameters were used to coat matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.
V. C. The following examples describe the detailed preparation of the non pH sensitive coating materials to be used to optionally delay the onset of action of any or all of the second, third, or additional dosage forms.

Example 47

Rupturable Film

| Component | Percentage (%) |
|---|---|
| Part A | |
| Cellulose Acetate 398-10 | 6.0 |
| PEG 400 | 1.5 |
| Acetone | 92.5 |

Step 1. Dissolve cellulose acetate in Acetone.
Step 2. Add TEC to Step 1, and allow to mix for 20 minutes.
Directions for Application of the Sustained Release Coating to the Beads:
Charge a wurster column equipped fluid bed with the beads to be coated. The beads must contain a component which will swell rapidly upon exposure to moisture. Beads containing croscarmellose sodium in Section I are good candidates as are beads with swellable hydrophilic polymers from Section IV. Spray the coating onto the beads at a rate and temperature known to those skilled in the art of bead coating so as to efficiently coat the beads to give a weight gain of between 4 and 20%. Dry the beads to the specified level of coating solvent for optimum handling and stability.
Coating Conditions for the Application of the Rupturable Film Coating.
The following coating parameters were used to coat matrix mini tablets from example 39 with the rupturable film coating. A 2.5% weight gain provided the desired lag time.

| Coating Equipment | Vector LDCS Coating System with 1.3 L pan |
|---|---|
| Spray nozzle diameter | 0.8 mm |
| Material Charge | 800 grams |
| Inlet Air Temperature | 40 to 45° C. |

| | |
|---|---|
| Outlet Air Temperature | 18 to 23° C. |
| Atomization Air Pressure | 25 psi |
| Pump Rate | 6 grams per minute |

The enteric coatings and non-pH sensitive coatings as described above can be applied to either a sustained release matrix bead as in examples 33-42, or to the immediate release component beads that have been previously treated with a sustained release coating, to thereby provide a sustained release bead with a delayed onset of action. In addition, the enteric coating or non-pH sensitive coating can be applied to the immediate release component bead directly to provide delayed onset of action.

VI. Final Composition

After all of the individual components are manufactured the final dosage form is assembled and may take the shape of a tablet, capsule or sachet. Preferably the final dosage form takes the shape of a capsule or tablet. Most preferably the final dosage form is a tablet.

The various dosage forms will be combined in the final dosage form in a ratio such that the Cmax is achieved in less than twelve hours after initiation of release of antibiotic and the product provides once a day coverage of anti-infective agent. Preferably the first, second, and third dosage forms provides 20-70%, 10-70%, and 10-70% of the total dosage form, respectively. More preferably the ratio of first, second and third dosage forms are in the range of 25-66%, 15-60%, and 15-60% of the total dosage form respectively. Most preferably the ratio of the first, second and third dosage forms are in the range of 33-60%, 25-50%, and 25-50%, respectively.

The present invention is particularly advantageous in that there is provided an antibiotic product which provides an improvement over twice a day administration of the antibiotic and an improvement over a once a day administration of the antibiotic.

Numerous modifications and variations of the present invention are possible in light of the above teachings, and therefore, within the scope of the appended claims the invention may be practiced otherwise than as particularly described.

What is claimed is:

1. A once-a-day antibiotic product comprising: first, second, and third dosage forms, each of said antibiotic dosage forms comprising at least one antibiotic and a pharmaceutically acceptable carrier, said first and second antibiotic dosage forms being a delayed release dosage forms, said third antibiotic dosage form being a delayed sustained release dosage form, wherein said third dosage form initiates release of antibiotic at about the same time as said second dosage form initiates release of antibiotic or wherein said third dosage form initiates release of antibiotic after said second dosage form initiates release of antibiotic, and wherein said second dosage form initiates release of antibiotic after said first dosage form initiates release of antibiotic, Cmax of the total antibiotic release from said antibiotic product is achieved in less than 12 hours from initial release of antibiotic, said once-a-day antibiotic product contains the total dosage of the at least one antibiotic for a twenty-four hour period, wherein said at least one antibiotic has a half life of 2-10 hours, and said once-a-day product is an oral dosage form and is free of immediate release dosage forms.

2. The product of claim 1, wherein said third dosage form initiates release of antibiotic at about the same time as said second dosage form initiates release of antibiotic.

3. The product of claim 1, wherein said third dosage form initiates release of antibiotic after said second dosage form initiates release of antibiotic.

4. The product of claim 1, wherein the Cmax for the product is reached no earlier than four hours after initial release of antibiotic.

5. The product of claim 1, wherein the antibiotic release from the first dosage form reaches a Cmax within from about 0.5 hours to about 2 hours after initial release of antibiotic.

6. The product of claim 1, wherein the antibiotic released from the second dosage form reaches a Cmax after Cmax is reached for the antibiotic released from the first dosage form.

7. The product of claim 1, wherein the antibiotic released from the third dosage form reaches a Cmax after Cmax is reached for the antibiotic released from the second dosage form.

8. The product of claim 1, wherein the first dosage form contains about 20-70% of the total dosage of antibiotic, the second dosage form contains about 10-70% of the total dosage of antibiotic, and the third dosage contains about 10-70% of the total dosage of antibiotic.

9. The product of claim 1, wherein the first dosage form contains about 25-66% of the total dosage of antibiotic, the second dosage form contains about 15-60% of the total dosage of antibiotic, and the third dosage form contains about 15-60% of the total dosage of antibiotic.

10. The product of claim 1, wherein the first dosage form contains about 33-60% of the total dosage of antibiotic, the second dosage form contains about 25-50% of the total dosage of antibiotic, and the third dosage form contains about 25-50% of the total dosage of antibiotic.

11. The product of claim 1 further comprising a fourth antibiotic dosage form, said fourth antibiotic dosage form being either a sustained or a delayed release dosage form and comprising at least one antibiotic and a pharmaceutically acceptable carrier and wherein said at least one antibiotic released from said fourth antibiotic dosage form reaches a Cmax after Cmax is achieved for antibiotic release from each of said first, second, and third dosage forms.

12. The product of claim 11, wherein the Cmax for the product is reached no earlier than four hours after initial release of antibiotic.

13. The product of claim 11, wherein the antibiotic released from the first dosage form reaches a Cmax within from about 0.5 hours to about 2 hours after initial release of antibiotic.

14. The product of claim 11, wherein the antibiotic released from the second dosage form reaches a Cmax in no more than 4 hours after initial release of antibiotic.

15. The product of claim 11, wherein the product is an oral dosage form.

16. The product of claim 11, wherein the antibiotic released from the second dosage form reaches a Cmax after Cmax is reached for the antibiotic released from the first dosage form.

17. The product of claim 11, wherein the antibiotic released from the third dosage form reaches a Cmax after Cmax is reached for the antibiotic released from the second dosage forms.

18. A process for treating a bacterial infection in a host comprising:
   administering to a host of antibiotic product of claim 1, once-a-day, 19. A process for treating a bacterial infection in a host comprising:
   administering to a host the antibiotic product of claim 2, once-a-day.

20. A process for treating a bacterial infection in a host comprising:

administering to a host the antibiotic product f claim 3, once-a-day.

21. A process for treating a bacterial infection in a host comprising:
administering to a host the antibiotic product of claim 4, once-a-day.

22. A process for treating a bacterial infection in a lost comprising:
administering to a host the antibiotic product of claim 5, once-a-day.

23. A process for treating a bacterial infection in a host comprising:
administering to a host the antibiotic product of claim 6, once-a-day.

24. A process for treating a bacterial infection in a host comprising:
administering to a host the antibiotic product of claim 7, once-a-day.

25. A process for treating a bacterial infection in a host comprising:
administering to a host the antibiotic product of claim 8, once-a-day, 26. A process for treating a bacterial infection in a host comprising:
administering to a host the antibiotic product of claim 9, once-a-day.

27. A process for treating a bacterial infection in a host comprising:
administering to a host the antibiotic product of claim 10, once-a-day 28. A process for treating a bacterial infection in a host comprising:
administering to a host the antibiotic product of claim 11, once-a-day.

29. A process for treating a bacterial infection in a host comprising:
administering to a host the antibiotic product of claim 12, once-a-day.

30. A process for treating a bacterial infection in a host comprising:
administering to a host the antibiotic product of claim 13, once-a-day.

31. A process for treating a bacterial infection in a host comprising:
administering to a host the antibiotic product of claim 14, once-a-day.

32. A process for treating a bacterial infection in a host comprising:
administering to a host the antibiotic product of claim 15, once-a-day.

33. A process for treating a bacterial infection in a host comprising:
administering to a host the antibiotic product of claim 16, at ,a-day.

34. A process for treating a bacterial infection in a host comprising:
administering to a host the antibiotic product of claim 17, once-a-day, 35. A once-a-day antibiotic product comprising: first, second, and third dosage forms, each of said antibiotic dosage forms comprising amoxicillin and pharmaceutically acceptable carrier, said first and second antibiotic dosage forms being a delayed release dosage forms, said third antibiotic dosage form being delayed sustained release dosage form, wherein said third dosage form initiates release of amoxicillin at about the same time as said second dosage form initiates release of amoxicillin or wherein said third dosage form initiates release of amoxicillin after said second dosage form initiates release of amoxicillin, and wherein said second dosage form initiates release of amoxicillin after said first dosage form initiates release of amoxicillin, Cmax of the total amoxicillin released from said antibiotic product is achieved in less than 12 hours from initial release of amoxicillin, said once-a-day antibiotic product contains the total dosage of amoxicillin for a twenty-four hour period, and said once-a-day product is an oral dosage form and is free of immediate release dosage forms.

36. A once-a-day antibiotic product comprising: first, second, and third dosage forms, each of said antibiotic dosage forms comprising azithromycin and a pharmaceutically acceptable carrier, said first and second antibiotic dosage forms being a delayed release dosage forms, said third antibiotic dosage form being a delayed sustained release dosage form, wherein said third dosage form initiates release of azithromycin at about the same ti e as said second dosage form initiates release of azithromycin car wherein said third dosage form initiates release of azithromycin after said second dosage form initiates release of azithromycin, and wherein said second dosage form initiates release of azithromycin after said first dosage form initiates release of a azithromycin, Cmax of the total azithromycin released from said antibiotic product is achieved in less than 12hours from initial release of azithromycin, said once-a-day antibiotic product contains the total dosage or azithromycin for a twenty-four hour period, and said once-a-day product is an oral dosage form and is free of immediate release dosage forms.

37. The product of claim 1, wherein the at least one antibiotic with a half life of 2-10 hours is ciprofloxacin, ceftibuten, or levofloxacin.

* * * * *